(12) United States Patent
Holliday

(10) Patent No.: US 8,518,030 B2
(45) Date of Patent: Aug. 27, 2013

(54) OUTPUT ENERGY CONTROL FOR LASERS

(75) Inventor: Keith Holliday, San Jose, CA (US)

(73) Assignee: AMO Manufacturing USA, LLC, Santa Ana, CA (US)

(*) Notice: Subject to any disclaimer, the term of this patent is extended or adjusted under 35 U.S.C. 154(b) by 2239 days.

(21) Appl. No.: 11/373,069

(22) Filed: Mar. 10, 2006

(65) Prior Publication Data

US 2007/0213697 A1 Sep. 13, 2007

(51) Int. Cl.
*A61F 9/008* (2006.01)

(52) U.S. Cl.
USPC .............................. 606/10; 606/11

(58) Field of Classification Search
USPC ................................ 606/4–6, 10, 11
See application file for complete search history.

(56) References Cited

U.S. PATENT DOCUMENTS

| | | | |
|---|---|---|---|
| 4,665,913 A | 5/1987 | L'Esperance, Jr. | |
| 5,097,291 A * | 3/1992 | Suzuki | 355/69 |
| 5,144,630 A | 9/1992 | Lin | |
| 5,282,014 A * | 1/1994 | Ruhl et al. | 356/4.02 |
| 5,646,791 A | 7/1997 | Glockler | |
| 5,683,379 A * | 11/1997 | Hohla | 606/5 |
| 5,713,892 A | 2/1998 | Shimmick | |
| 5,742,626 A * | 4/1998 | Mead et al. | 372/22 |
| 5,878,068 A * | 3/1999 | Mitarai et al. | 372/30 |
| 5,912,779 A * | 6/1999 | Llewellyn et al. | 360/55 |
| 6,005,879 A | 12/1999 | Sandstrom et al. | |
| 6,008,497 A * | 12/1999 | Mizoguchi et al. | 250/492.1 |
| 6,067,306 A | 5/2000 | Sandstrom et al. | |
| 6,203,539 B1 | 3/2001 | Shimmick et al. | |
| 6,245,059 B1 | 6/2001 | Clapham | |
| 6,280,435 B1 | 8/2001 | Odrich et al. | |
| 6,319,247 B1 | 11/2001 | Hofer et al. | |
| 6,347,549 B1 | 2/2002 | Ryan et al. | |
| 6,671,294 B2 | 12/2003 | Kroyan et al. | |
| 6,673,062 B2 | 1/2004 | Yee et al. | |
| 6,727,731 B1 | 4/2004 | Rebhan et al. | |
| 6,865,212 B2 * | 3/2005 | Kleinschmidt | 372/57 |
| 6,914,920 B2 | 7/2005 | Kleinschmidt | |
| 7,057,705 B2 * | 6/2006 | Heintze | 355/53 |
| 2001/0056276 A1 * | 12/2001 | LaHaye | 606/5 |
| 2002/0057724 A1 * | 5/2002 | Vogler et al. | 372/58 |
| 2004/0021840 A1 * | 2/2004 | Heintze | 355/30 |
| 2005/0021011 A1 * | 1/2005 | LaHaye | 606/5 |
| 2005/0203494 A1 | 9/2005 | Holliday | |

OTHER PUBLICATIONS

U.S. Appl. No. 08/468,898, filed Jun. 6, 1995.

* cited by examiner

*Primary Examiner* — Bill Thomson
*Assistant Examiner* — Jeffrey Lipitz
(74) *Attorney, Agent, or Firm* — AMO Manufacturing USA, LLC

(57) ABSTRACT

Devices, systems, and methods control pulse energies of excimer and other lasers, particularly for refractive correction in which a pulse rate, pulse energy, or other parameters of a pulsed laser is varied during use. A calibration laser mode may be used to fire a series of laser pulses to characterize a correlation between laser energy and a laser operation parameter (typically discharge high voltage) throughout a range. During an operation mode, subsequent voltages may be set based on energies of prior pulses while accounting for a curve or change in rate of the correlation.

6 Claims, 8 Drawing Sheets

OUTPUT ENERGY CONTROL FOR LASERS

BACKGROUND OF THE INVENTION

The present invention generally relates to methods, systems, and devices for controlling lasers, and is particularly useful for controlling pulse energies of excimer lasers during laser eye surgery.

Known laser eye surgery procedures generally employ an ultraviolet or infrared laser to remove a microscopic layer of stromal tissue from the cornea of the eye so as to alter the refractive characteristics of the eye. The laser typically removes a selected shape of the corneal tissue, often to correct refractive errors of the eye. Ultraviolet laser ablation can result in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and movable apertures, controlled scanning systems, eye movement tracking mechanisms, and the like. In known laser systems, the laser beam often comprises a series of discrete pulses of laser light energy, with the total shape and amount of tissue removed being determined by the shape, size, location, and/or number of laser energy pulses including in a pattern of pulses directed onto the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, frequency multiplied solid-state lasers, and the like.

Known corneal correction treatment methods have generally been successful in correcting standard vision errors including myopia, hyperopia, astigmatism, and the like. More recently, highly accurate measurements of defects or irregularities in the optical system of the eye have been made widely available. Wavefront measurements of the eye identify irregular aberrations of the eye with sufficient accuracy to allow a customized ablation pattern to be developed. By customizing the refractive procedure to the specific defects of a patient's eye, it is often possible to correct irregular minor aberrations reliably and repeatedly, often providing visual acuities after treatment of better than 20/20.

As with many advances, still further improvements in laser eye surgery methods would be desirable. For example, as the accuracy of wavefront aberration measurements and general laser surgical techniques has increased, the benefits of more and more precise control over the distribution of laser energy over the eye has also grown. Work in connection with the present invention has determined that improvements in devices, systems, and methods for controlling the energies of light pulses generated by the laser may increase the accuracy of a refractive procedure.

Excimer lasers have been used for a number of years in a variety of industrial processes, and while the laser pulse energy control systems derived from industrial excimer laser controllers and/or previously developed for refractive resculpting have helped allow the rapid growth in laser eye surgery to date, additional improvements may benefit from a recognition of the differences between the uses of excimer lasers in industrial processing and their use in laser eye surgery systems. For example, many laser eye surgery systems employ optical components which move during the surgical procedure so as to distribute the laser energy across the cornea. The firing rate of the laser for the individual pulses may vary somewhat to accommodate this movement, and the like. Additionally, the total time during a refractive procedure may be significantly shorter than the timeframes in which industrial excimer lasers run. These and other differences between the use and structures of laser eye surgery systems and industrial laser devices indicate that benefits may be available by providing improved and/or specialized devices, systems, and methods for controlling lasers for use in laser eye surgery.

In light of the above, it would generally be beneficial to provide improved devices, systems, and methods for controlling lasers, particularly for controlling excimer lasers used in laser eye surgery systems. It would be helpful if these improved techniques could enhance the accuracy and reliability of laser eye surgery without significantly increasing the complexity or cost of the treatments, and ideally by taking advantage of components which have already been developed and are now included in many laser eye surgery systems.

BRIEF SUMMARY OF THE INVENTION

The present invention generally provides improved devices, systems, and methods for controlling laser energies, and particularly for controlling the pulse energies of excimer and other lasers used in laser eye surgery (and for other applications). Embodiments of the present invention may be suitable for use in procedures in which a pulse rate of a pulsed laser varies during use, or in which other laser operation parameters (such as pulse energy) will vary during use, but in which it is desirable to continue to maintain accurate control over the energy of the laser. Such embodiments may be particularly well suited to refractive and other procedures in which the total operating time between starting of the laser pulses and shutting off of the laser is less than about 10 minutes. By implementing a calibration laser mode in addition to a standard operating mode, and by accurately characterizing a relationship or correlation between laser energy pulses and a laser operation parameter such as the high voltage used to fire the pulse (V) throughout a range that encompasses a curve in the correlation, such embodiments may increase the accuracy of laser pulse energy control, often while making use of components and structures that are included in many commercial laser eye surgery systems.

In a first aspect, the invention provides a method for controlling a pulsed laser. The method comprises firing the laser to produce a series of laser pulses. A correlation between energy of the pulses and voltages of the laser are generated, the correlation defining differing rates of change in pulse energy with changes in voltage. A first pulse is generated by the laser by applying a first voltage to the laser. A second voltage is determined for the laser so as to generate a second pulse with a desired pulse energy using the correlation.

The correlation may optionally comprise a quadratic relationship between pulse energy E and a discharge high voltage V of the laser. The quadratic relationship may optionally be in the form:

$$E = c_1 V^2 + c_2 V + c_3;$$

in which $c_1$, $c_2$, and $c_3$ are constants. The second voltage may be determined by identifying a desired change in energy ΔE between the energy of the first pulse and the desired energy, and by identifying an appropriate change in voltage from the correlation using the first voltage. Variations in the voltage may be damped according to a damping factor.

The series of laser pulses from which the correlation is generated may be fired by the laser using at least four differing voltages. In many embodiments, a plurality of pulses may be fired at each voltage, with the pulses at each voltage being averaged and the correlation being determined using the average pulse energies.

In many embodiments, the laser will comprise an excimer laser. The series of pulses may be fired while the laser is operating in a calibration mode, prior to transmitting pulses onto a target surface. The first and second laser pulses may be directed onto the target surface while the laser is operating in an operating mode. A firing rate of the laser may vary while the laser is in the operating mode. The laser may remain in the operating mode for less than about 10 minutes, often for about 5 minutes or less. The target surface may be disposed on the corneal tissue, with the operating mode effecting resculpting of the corneal tissue so as to alter optical characteristics of the eye. The laser may be operated in the calibration mode before treatment of each eye or after every few eyes, prior to treatment of each patient, or prior to use each day, weekly, monthly, or the like.

In another aspect, the invention provides a pulsed laser system comprising a laser for producing a series of laser pulses. An energy sensor may be disposed along an optical path of the laser, with the energy sensor transmitting signals in response to pulse energies of the pulses. A driving circuit may be coupled to the circuit so as to apply voltage thereto in response to command signals. The energies of the pulses may vary with the voltages applied to the laser. A processor may be coupled to the driving circuit, with the processor having a correlation defining differing rates of change in pulse energies with changes in the voltages. The processor may generate the command signals in response to the correlation.

The processor will often comprise machine readable programming instructions or code embodying the correlation. The programming instructions may also be configured for determining a second voltage by identifying a desired change in energy $\Delta E$ between the energy of a first pulse and a desired pulse energy, and by identifying an appropriate change in voltage from the correlation using the first voltage. In an exemplary embodiment, the correlation may comprise a quadratic relationship between the pulse energy E and the discharge high voltage V of the laser, with an exemplary quadratic relationship being in the form $E=c_1 V^2 + c_2 V + c_3$, in which $c_1$, $c_2$, and $c_3$ are constants that are determined from recorded pulse energies. The processor may further comprise programming instructions for effecting one or more of the method elements described herein.

In another aspect, the invention provides a programmable code product for use with a laser system. The laser system may have a laser for producing a series of laser pulses, an energy sensor disposed along an optical path of the laser, a driving circuit coupled to the laser so as to apply voltage thereto, and a processor coupling the sensor to the driving circuit per the programmable code product. The programmable code product may comprise machine readable programming code embodying instructions for generating a correlation between the energies of the pulses and voltages of the laser, the correlation defining differing rates of change in pulse energy with changes in voltage. The programmable code product may also comprise machine readable programming code embodying instructions for determining a voltage for the laser so as to generate a pulse with a desired pulse energy using the correlation.

The programmable code product may be embodied in a tangible media, and/or may be transmitted to the processor using a communication link, input device, or the like. The programmable code product may further comprise programming instructions embodying code for effecting any of the method elements described herein.

DETAILED DESCRIPTION OF THE INVENTION

The present invention generally provides improved devices, systems, and methods for controlling output energy of a laser. Embodiments of the present invention may be particularly useful for enhancing the accuracy and efficacy of control over pulse energies of excimer lasers used in laser eye surgical procedures, such as photorefractive keratectomy (PRK), phototherapeutic keratectomy (PTK), laser assisted in situ keratomileusis (LASIK), laser epithelial keratomileusis (LASEK), and the like. In some embodiments, the present invention may provide enhanced accuracy of refractive procedures by improving the precision with which corneal tissues are removed during a refractive treatment program.

While the systems and methods of the present invention may be described herein primarily in the context of laser eye surgery systems, techniques of the present invention may also be adapted for use in alternative eye treatment procedures and systems including ablatable intraocular lenses, contact lenses, and the like. Additionally, embodiments of the invention may be used outside of eye treatment for enhancing laser devices used for a wide variety of purposes, particularly where pulsed laser devices are employed.

The techniques described herein may be readily adapted for use with a wide variety of existing laser systems. By enhancing control over the pulse energies of the laser pulses delivered within a pattern so as to alter the refractive properties of a patient's eye, the invention may facilitate and/or improve sculpting of the cornea so that treated eyes regularly exceed a 20/20 threshold of visual acuity.

Figure 1:
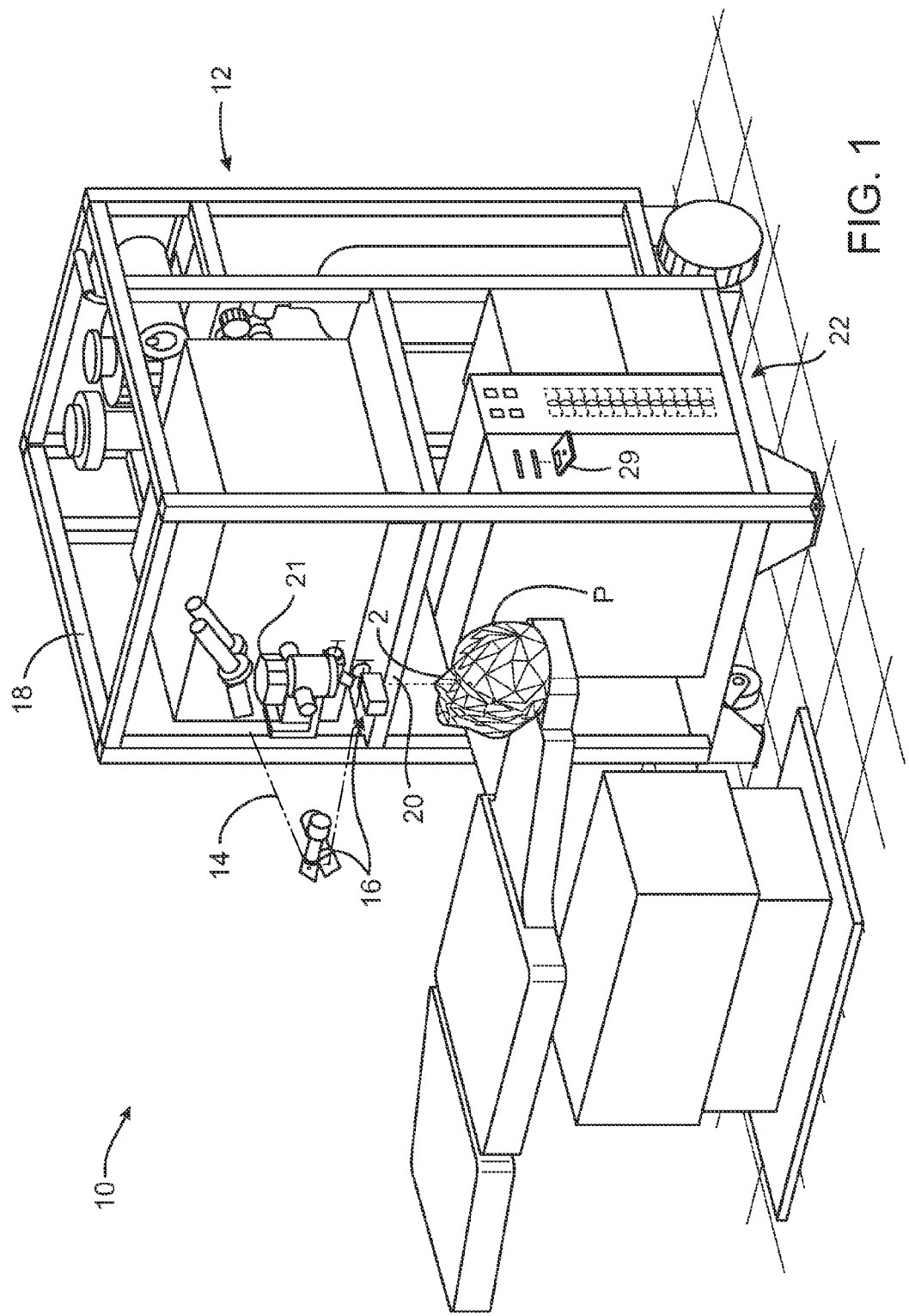
FIG. 1 schematically illustrates a laser eye surgery system embodying aspects of the present invention.

Referring now to FIG. 1, a laser eye surgery system 10 for incorporating the present invention includes a laser 12 that produces a laser beam 14. Laser delivery optics 16 are in a path of laser beam 14. Delivery optics 16 direct laser beam 14 to an eye of a patient P. A delivery optics support structure (not shown here for clarity) extends from a frame 18 supporting laser 12. An input device 20 is used to align laser system 10 in relation to an eye of a patient P. A microscope 21 is mounted on the delivery optics support structure, the microscope often being used to image a cornea of an eye. In various embodiments, a laser eye surgery system 10 includes at least some portions of a VISX Excimer Laser System available from VISX, INCORPORATED of Santa Clara, Calif.

While an input device 20 is here schematically illustrated as a joystick, a variety of input components may be used. Suitable input components may include trackballs, touch screens, or a wide variety of alternative pointing devices. Still further alternative input components include keypads, data transmission mechanisms such as an Ethernet, intranet, Internet, a modem, or the like.

Laser 12 generally comprises an excimer laser and ideally comprises an argon-fluoride laser producing pulses of laser light having a wavelength of approximately 193 nm. Each pulse of laser light typically has a fixed pulse duration having a full width half maximum (FWHM) of about 15 nanoseconds during a treatment. Laser 12 is preferably designed to provide a feedback stabilized fluence at the patient's eye, delivered via delivery optics 16. The present invention may also be useful with alternative sources of electromagnetic radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), and/or solid state lasers, including frequency multiplied solid state lasers such as flash-lamp and diode pumped solid state lasers. Exemplary solid state lasers include UV solid state lasers (approximately 193-215 nm) such as those described in U.S. Pat. Nos. 5,144,630 and 5,742,626. Hence, although an excimer laser is the illustrative source of the ablating beam, other lasers may be used.

Laser 12 and delivery optics 16 will generally direct laser beam 14 to an eye of patient P under direction of a processor 22. Processor 22 will often selectively adjust laser beam 14 to expose portions of the cornea to pulses of laser energy so as to effect a predetermined sculpting of a cornea and alter refractive characteristics of the eye. In many embodiments, both laser 14 and laser delivery optical system 16 will be under computer control of processor 22 to effect the desired laser sculpting process, with processor 22 effecting (and optionally modifying) a pattern of laser pulses. The pattern of pulses may by summarized in a treatment table listing of machine readable data of a tangible media 29.

Laser beam 14 may be adjusted to produce a desired sculpting using a variety of alternative mechanisms. For example, laser beam 14 may be selectively limited using one or more variable apertures, and an exemplary variable aperture system having a variable iris and a variable width slit is described in U.S. Pat. No. 5,713,892, the full disclosure of which is incorporated herein by reference. The laser beam may also be tailored by varying a size and offset of a laser spot from an axis of an eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning the laser beam over a surface of an eye and controlling a number of pulses and/or dwell time at each location, as described, for example, by U.S. Pat. No. 4,665,913 (the full disclosure of which is incorporated herein by reference) and as may be embodied in laser systems by Alcon, Bausch & Lomb, Wavelight and the like; using masks in an optical path of laser beam 14 which ablate to vary a profile of a beam incident on a cornea as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea as described in U.S. Pat. Nos. 6,319,247; 6,280,435; and 6,203,539, the full disclosures of which are incorporated herein by reference; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. Nos. 5,646,791 and 5,912,779 the full disclosures of which are incorporated herein by reference.

Processor 22 may comprise (or interface with) a conventional PC system including standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29, which may embody machine-readable instructions for any of the methods described herein. Tangible storage media 29 may comprise a floppy disk, an optical disk, a data tape, a volatile or non-volatile memory, or the like, and processor 22 will include memory boards and other standard components of modem computer systems for storing and executing computer program code. Tangible storage media 29 may optionally embody wavefront sensor data, wavefront gradients, a wavefront elevation map, a treatment map, a corneal topography map, a measurement of a refraction of an eye, an ablation table, and/or instructions to adjust the amount of energy.

Figure 2:
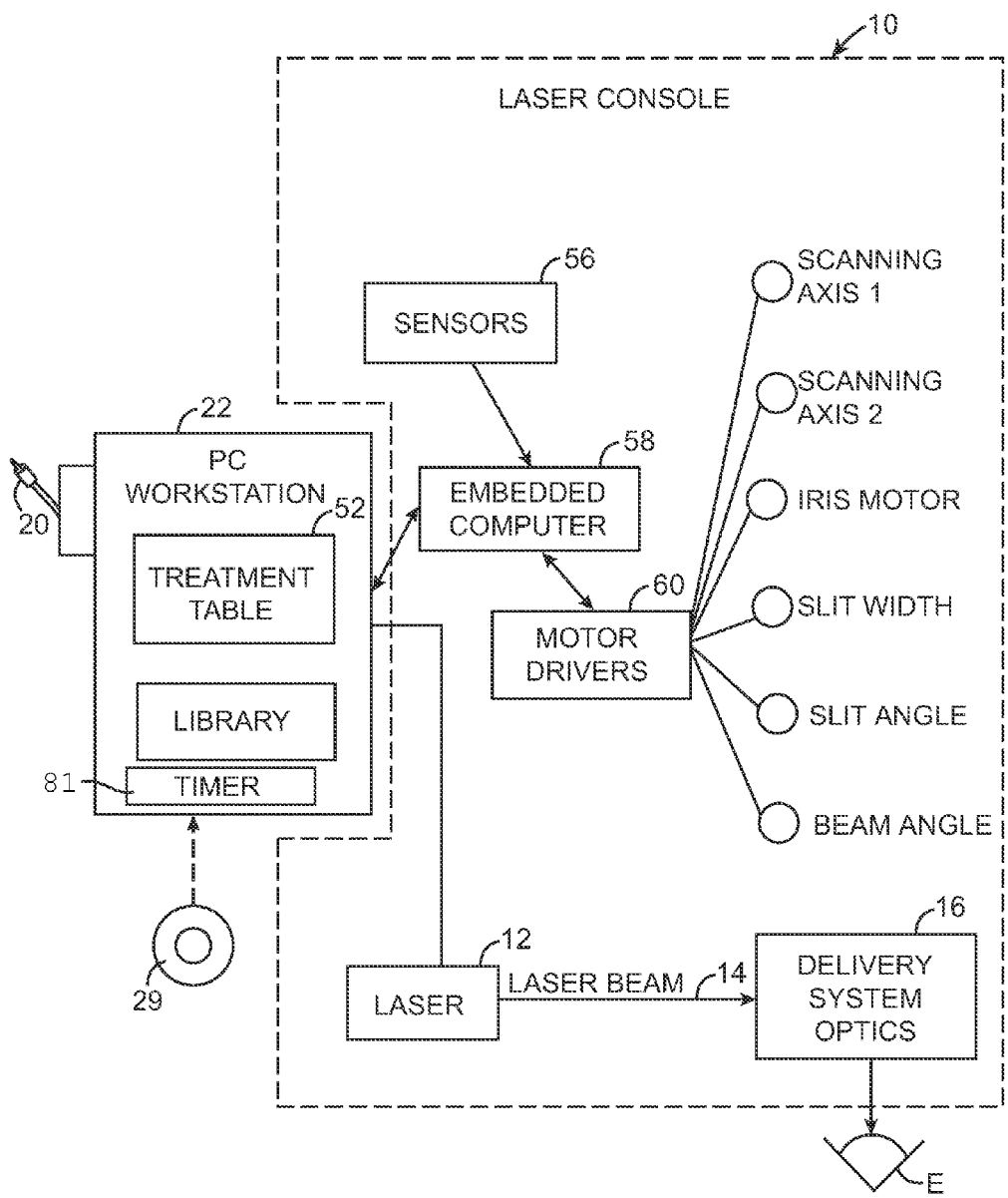
FIG. 2 schematically illustrates a functional block diagram for one control architecture of an ablation system.

Referring now to FIG. 2, a control system of a laser system 10 is schematically illustrated. Processor 22 enables precise control of laser system 10 to sculpt a surface shape according to a laser treatment table 52. Processor 22, which generally comprises a PC workstation, makes use of a computer program stored on tangible media 29 to generate treatment table 52, as described in U.S. Pat. No. 6,673,062, the full disclosure of which is incorporated herein by reference. Processor 22 includes a library 44 of treatments as described in U.S. Pat. No. 6,245,059, the full disclosure of which is also incorporated herein by reference. An embedded computer 58 within laser system 10 is in electronic communication with the PC workstation. Alternatively, a PC workstation may be embedded in laser system 10 and include an embedded processor card in communication with a PC workstation for directing an ophthalmic surgery. Processing may all be performed centrally by a single processor executing a single program or may be distributed among a large number of processing circuits running separate code or subroutines in a wide variety of data processing and code architectures. Hence, devices and methods described herein as employing a processor to run a program may encompass multiple processes running multiple programs.

Embedded computer 58 is in electronic communication with a plurality of sensors 56 and a plurality of motor drivers 60. Motor drivers 60 are coupled to embedded computer 58 to vary a position and/or configuration of the optical components of delivery optics 16 according to treatment table 52. For example, motor drivers 60 may drive first and second scanning axes to control a position of an offset lens or one or more scanning mirrors to move the beam (optionally after separation of the beam into several laser beamlets) over a surface of a cornea. Other driver motors may optionally be used to control an iris diaphragm to vary an overall diameter of the beam, one or more shutters to block the beam, and the like. A timer 81 controls a time interval between pulses, and processor 22 can issues commands for laser 12 to generate each pulse of laser beam 14. A wide variety of drivers may be used to direct a desired pattern of laser energy onto the cornea.

Figure 3:
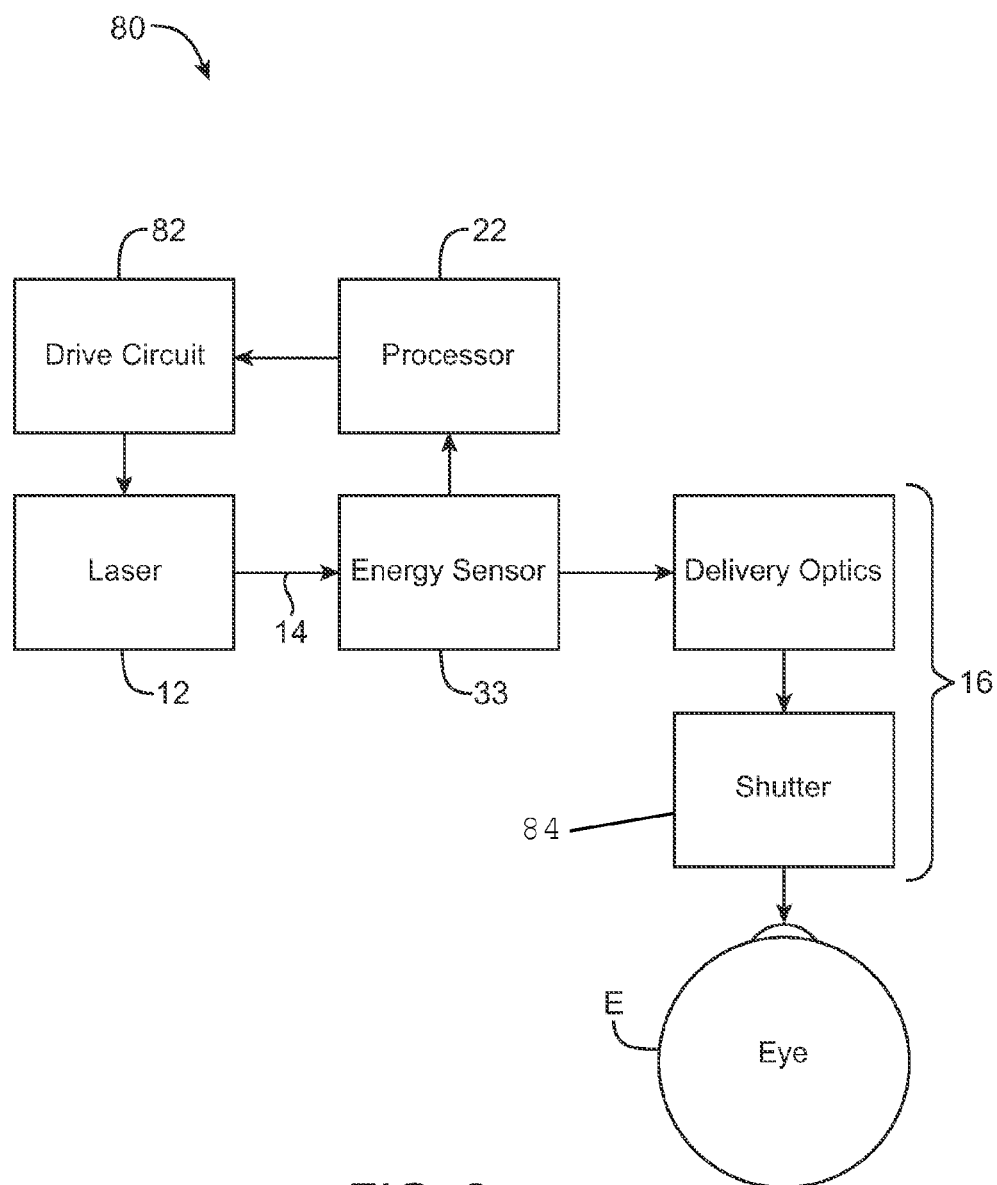
FIG. 3 schematically illustrates a functional block diagram with components of an exemplary embodiment of an output energy control for a refractive excimer laser.
Figure 4:
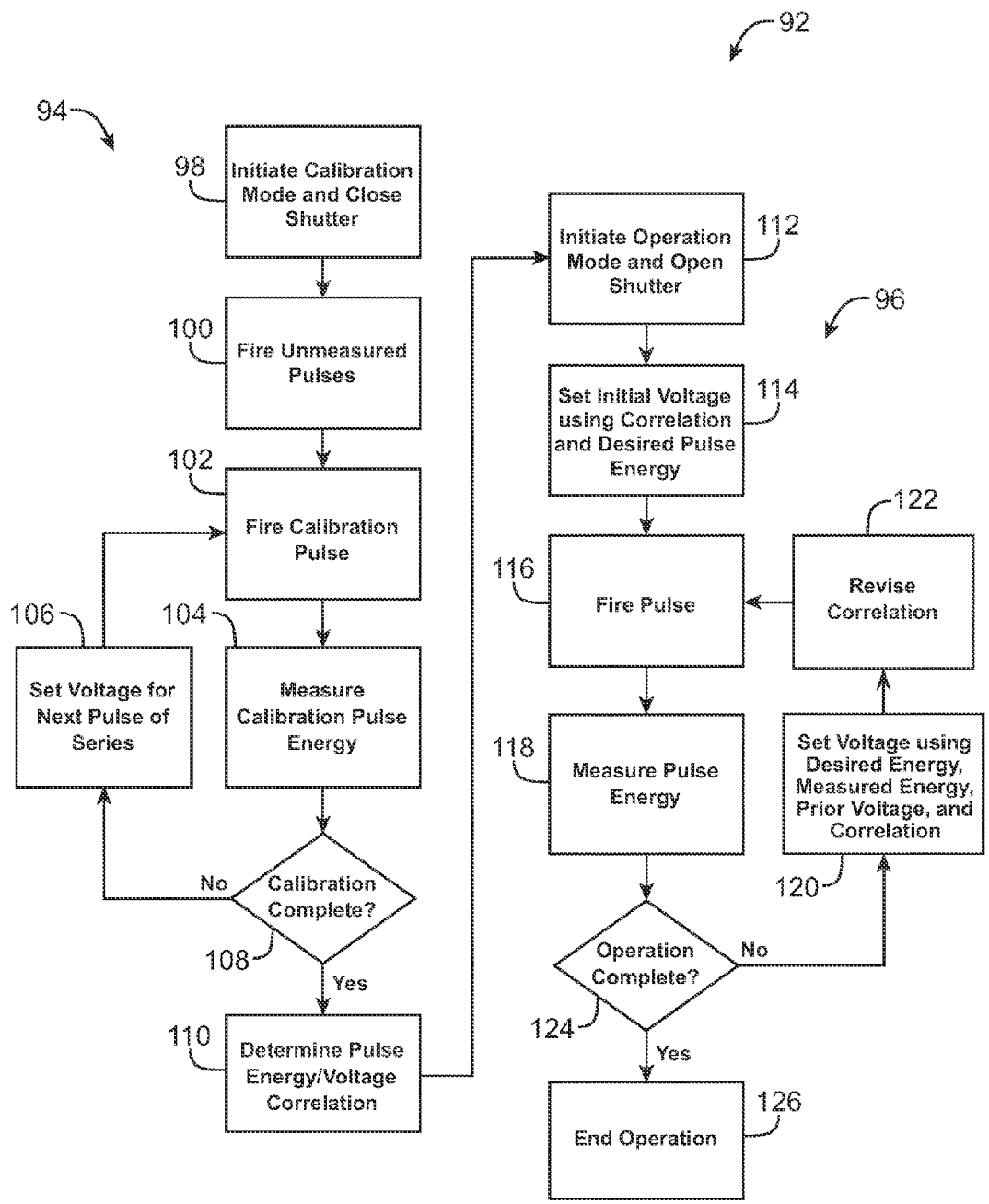
FIG. 4 is a flow chart schematically illustrating an embodiment of a method for output energy control of a refractive excimer laser, in which the method includes a calibration mode and an operation mode.

As can be understood with reference to FIGS. 3 and 4, in many embodiments, processor 22 may be used to calculate adjustments to an operating parameter of the laser such as discharge high voltage or the like, often in response to signals from a measurement device 33. Processor 22 may generate command signals per such calculations, with the command signals being transmitted to a driving circuit of a laser 12, and so that the driving circuit applies a voltage per the command signals. Processor 22 will also often control operation of laser 12 in both a calibration mode and an operation mode, with the calibration mode generally being used to determine a correlation between laser pulse energies (as sensed by measurement device 33) and one or more operating parameters of laser 12 (such as discharge high voltage). A computer program for use by processor 22 will often be stored on tangible medium 29 to make such calculations, and/or the computer program may be stored in a random access memory (RAM), read-only memory (ROM), or may be transmitted to processor 22 using a communication link such as an internet, an intranet, an Ethernet, a wireless communication network, or the like. Tangible medium 29 may comprise a magnetic recording media (such as a floppy disk, a hard disk, a magnetic tape, or the like), an optical recording media (such as a CD, a DVD, or the like), a flash memory (such as a USB flash memory device) or the like. The computer program will typically comprise a machine-readable code of programming instructions for implementing one or more of the methods described herein.

Referring to FIG. 3, laser beam delivery system 16 is often optically coupled to an energy measurement sensor or device 33 for measuring the energy of the pulses of the laser beam that are transmitted toward the eye E. Measurement device 33 will generally be disposed along the optical path of the laser beam from laser 12, often being disposed upstream of some or all of the optical components of delivery optics 16 near (and for enhanced accuracy, immediately adjacent to) the output of the laser. Alternative embodiments may make use of energy sensors which are downstream of some, most, or even all of the delivery optics. Exemplary laser energy sensing measurement devices may comprise transmissive low insertion loss probes, which may optionally include a florescent material disposed with the optical path of laser beam 14. Suitable sensing devices may be commercially available from Star Tech Instruments of Connecticut as model VHR-AR, optionally with appropriate modifications for a specific laser eye surgery system. A wide variety of alternative energy sensors might also be employed, including those coupled to the laser via a semi-translucent mirror, lens, or the like, to allow some amount of laser beam 14 to be transmitted to the energy measurement device 33, while the remainder of the laser energy is directed onto the eye.

In many cases, measurement device 33 may be used before laser beam 14 is applied to eye E. For example, a sequence of pulses of the laser beam may be fired at a target positioned at the location which will be occupied by eye E during a laser eye surgery procedure. While the sequence of test pulses is fired at the test target, measurement device 33 measures the amount of energy that will be delivered to the patient with each pulse during the sequence. In other embodiments, a shutter may be disposed along the optical path between the mirror through which light is transmitted to measurement device 33 and eye E, so that at least some pulses may be blocked by the shutter while their energy is measured. The delivery path of laser beam 14 is depicted in FIG. 2 by the line labeled as laser beam 14. The delivery path is generally a path along which a laser beam may (at least in some operating mode) travel from a laser beam generating device such as a laser toward one or more targets.

Referring now to FIG. 3, a laser energy control system 80 typically employs measurement device 33 to provide signals to processor 22 in response to an energy of the laser pulses of laser beam 14. Processor 22 transmits command signals to a drive circuit 82, which applies an appropriate voltage to laser 12, providing an effective feedback loop of the laser energy. A shutter 84 of delivery system 16 may optionally block laser beam 14 from reaching eye E, with the shutter again typically operating per the command of processor 22.

Laser energy control system 80 generally causes the laser 12 to output ultraviolet pulses at a controlled energy throughout a refractive treatment of the eye. This control may be effected with or without other laser energy control systems and methods, including those described in U.S. application Ser. No. 11/077,173, filed on Mar. 9, 2005 and entitled "Stabilizing Delivered Laser Energy", the full disclosure of which is incorporated herein by reference.

In many refractive laser eye treatments, laser 12 may fire at a repetition rate that varies during treatment of eye E. Such varying of the firing rate may cause the laser performance and laser energy to also vary. For example, firing of laser 12 at higher repetition rates may generally involve higher values of discharge high voltage (V) being applied to the laser by drive circuit 82. Variation in laser energy may also result from variations in the excimer gas mixture, the time or treatment count since excimer gases have been replaced, and the like. Hence, laser energy control system 80 may be responsive to changes in a variety of operating conditions of the laser eye surgery system.

While laser energy control system 80 may include a full proportional, integral, and derivative (PID) control loop, many embodiments may use a subset of proportional/integral/derivative parameters to provide effective control. For example, only a proportional control may be implemented in some embodiments. Selection of appropriate proportional control parameters may help ensure stable energies, avoiding unstable oscillations (for example) by responding somewhat slowly to changes in laser pulse energy. As a result, a number of pulses may be fired by laser 12 before reaching a target laser pulse energy, with often more than 10 pulses being fired, and in one embodiment about 30 pulses being fired before laser energy control system 80 provides a target pulse energy. Other embodiments may achieve desired pulse energies with significantly fewer pulses by appropriate selection of different proportional constants, in some cases achieving target energies in fewer than 5 pulses, although some such embodiments may present an increased risk of instability if the relationship between the high discharge voltage V and laser beam pulse energy E changes.

In some embodiment, pulse energy control system 80 may measure the dependence of the laser pulse energies generated by laser 12 on discharge high voltage V before each patient is treated. The data collected is stored and used to update a correlation included in processor 22. This allows laser 12 to be adjusted quickly so as to provide the desired laser energies without instability or laser energy oscillations. Once the correlation between laser energy and discharge high voltage are established, processor 22 makes use of this information during operation of the laser 12 so as to treat eye E. To enhance the accuracy of refractive corrections, the calibration is performed during a calibration mode in which shutter 84 is closed, and/or in which eye E is otherwise not disposed in the optical path from the laser. Once the correlation has been established, laser 12 is operated in an operation mode so as to treat eye E.

Referring now to FIG. 4, a laser energy control method 92 generally includes a calibration mode 94 and an operation mode 96. The calibration mode generally involves firing of the laser without allowing the laser energy to reach the target surface of the eye so as to generate a correlation between laser energy and voltage of the laser. The operation mode generally makes use of the correlation so as to provide a desired laser energy at the target tissue of the eye. In exemplary method 92, calibration mode 94 precedes operation mode 96, with the calibration mode preferably occurring less than half an hour prior to the associated operation mode, and with the calibration mode ideally being completed less than a minute prior to initiation of the operation mode. Other embodiments may perform at least a portion of the calibration mode after initiation of the operation mode, optionally by blocking the laser energy from reaching the eye for at least some laser pulses after initiation of operation mode 96. Refinement of the correlation may also continue after initiation of and during operation mode 96.

Calibration mode 94 is initiated and transmission of laser energy along the optical path to the tissues of the eye are prevented, optionally by closing the shutter 98, positioning a test ablation plastic in the eye treatment location, or the like. The laser begins firing a series of unmeasured pulses 100 so as to avoid spurious effects of laser startup, transients, and the like from altering or degrading the correlation. The unmeasured pulses may comprise, for example, less than about 50 pulses, optionally comprising 10 pulses.

With the discharge high voltage set at an initial value, the laser is fired 102 and the pulse energy is measured and recorded 104. Firing of the laser is repeated throughout a measured calibration pulse series, with the discharge high voltage being changed 106 between at least some of the pulses of the calibration series. It should be noted that a number of measured calibration pulses (for example, less than about 20, and optionally being 5) may be fired at each desired discharge high voltage, with the firing of the laser often being performed with a repetition rate that is typical for the laser during a refractive treatment (for example, at between 10 and 200 Hz, optionally being at 20 Hz). The average pulse energy of the pulses at that discharge high voltage can then be calculated, with the voltage being adjusted 106 and another series of pulses being fired at the next discharge high voltage.

Once the complete series of calibration pulses has been fired 108, the pulse energy/voltage correlation may be determined 110, ideally from four or more different measured or averaged laser pulse energies at differing discharge high voltages. Six or more differing discharge high voltages will often be used, and ideally the correlation will be determined using nine or more differing discharge high voltages. The exemplary correlation comprises a best fit quadratic formula of the form:

$$E = c_1 V^2 + c_2 V + c_3;$$

where E is the pulse energy, V is the discharge high voltage (V), and $c_1$, $c_2$, and $c_3$ are fitting parameters or constants determined from the pulse energy data. Some or all of the constants may be negative, although $c_1$ will often be positive and $c_2$ negative. Operation mode 96 may optionally employ parameters or constants relating to the rate of change of energy output with changes in high discharge voltage, and as this is effectively a differential of the above quadratic equation, in many embodiments the constant parameters $c_1$ and $c_2$ may be the only constants from the above equation that are used in the calculation of voltages in operation mode 96. The rate of change in energy will often refer to the changes in pulse energy for changes in high discharge voltage, for example, the number of additional volts to obtain one additional mJ of extra pulse energy or the number of additional mJ of pulse energy from one additional volt, rather than a time-based rate.

Referring still to FIG. 4, operation mode 96 is generally initiated and the optical path is allowed to extend to a target tissue of the eye 112, often by opening the shutter and/or positioning the patient. An initial voltage for the operation mode is set 114, optionally using the correlation, by using a standard initial voltage, or the like. The laser is fired 116 and the pulse energy measured 118. The voltage is reset using the correlation 120, and the correlation may optionally be revised 122 using the information available by prior firing of the laser during the operation mode and in the exemplary embodiment using one or more known discharge high voltages and the one or more resulting recorded pulse energies.

In the exemplary embodiment, voltage is set 120 during operation mode 92 using (along with the correlation derived during calibration mode 94) the desired energy, the measured pulse energy 116, the prior voltages that were set 114, and/or the like. An exemplary calculation of a new voltage $V_{new}$ from the previous voltage $V_{old}$ and $\Delta E$ (the energy difference between the desired or target energy and the actual energy of the prior pulse) employs the following formula:

$$V_{new} = V_{old} + \frac{\Delta E}{2c_1 V_{old} + c_2}$$

The additional voltage desired for the next pulse is the desired change in energy multiplied by the energy change rate identified from the correlation, for example, the number of volts to increase the energy by 1 mJ. This additional voltage is also equivalent to the desired change in energy divided by the increase in energy (for example, in mJ) obtained by increasing discharge high voltage 1 volt. The rate of change of the energy output with respect to V is the differential of the above equation, and is given by:

$$\frac{dE}{dV} = 2c_1 V + c_2$$

which is the denominator of the prior equation.

In many embodiments, it may be desirable to add a damping parameter or factor to avoid oscillations or other instabilities of the laser due to line of fluctuations in pulse energy, measurement error, or other noise. Damping factor D may be included as follows:

$$V_{new} = V_{old} + D \cdot \frac{\Delta E}{2c_1 V_{old} + c_2}$$

with the exemplary damping factor being in a range from 0.25 to 1, optionally being from 0.5 to 1, with lower values generally causing the system to have a slower response to changes in target energy and less shot-to-shot noise, and with larger values generally causing the system to be faster in responding in changes to target energy, often with somewhat greater shot-to-shot noise. Exemplary embodiments may employ damping factors of 0.5, 1, or the like. The calculation of a new voltage $V_{new}$ may be performed to set the high discharge voltage for each pulse. Other embodiments may average pulse energies from a plurality of prior pulses, calculate new discharge voltages only after a plurality of pulses (optionally within an acceptable energy range), or the like. Once the refractive correction is completed 124, the operation mode 96 is terminated 126, with a new calibration mode 94 optionally being initiated only for the next patient.

Figure 5:
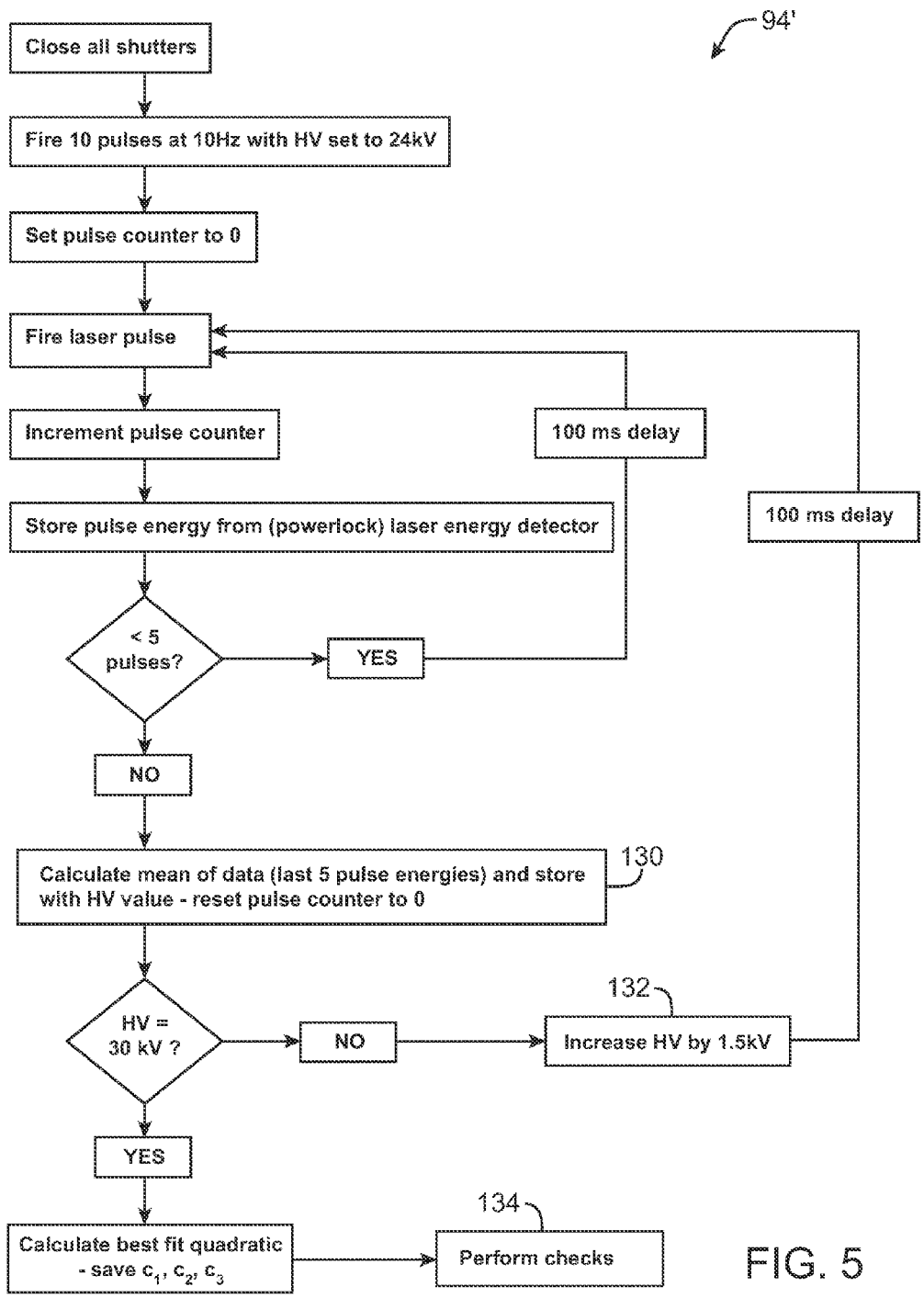
FIG. 5 is a flow chart schematically illustrating a more detailed embodiment of a calibration mode for an output energy control for a refractive excimer laser.

Referring now to FIG. 5, a more detailed calibration mode methodology 94' shows specific steps that can be used to generate average pulse energies at a given voltage 130, an exemplary voltage increment 132 approach so as to provide calibration high discharge voltages throughout a range from about 24 kV to about 30 kV, and the like. Detailed calibration methodology 94' also includes data checks 134, which may include verifying that the average pulse energies are within a reasonable expected value (such as between about 80 and 250 mJ), that the correlation (specifically the quadratic fit) is reasonable (with energy values being between about 90 and 150% of that of the energy measured from the smaller adjacent high discharge voltage), that the top one or two voltages generate greater energies than the lowest one or two voltages, that all data points are within a reasonable ration (for example 10%) of the correlation curve fit, that calculated energies based on the correlation are greater for at least some of the higher voltage values than for at least some of the lower voltage values, and the like.

Figure 6:
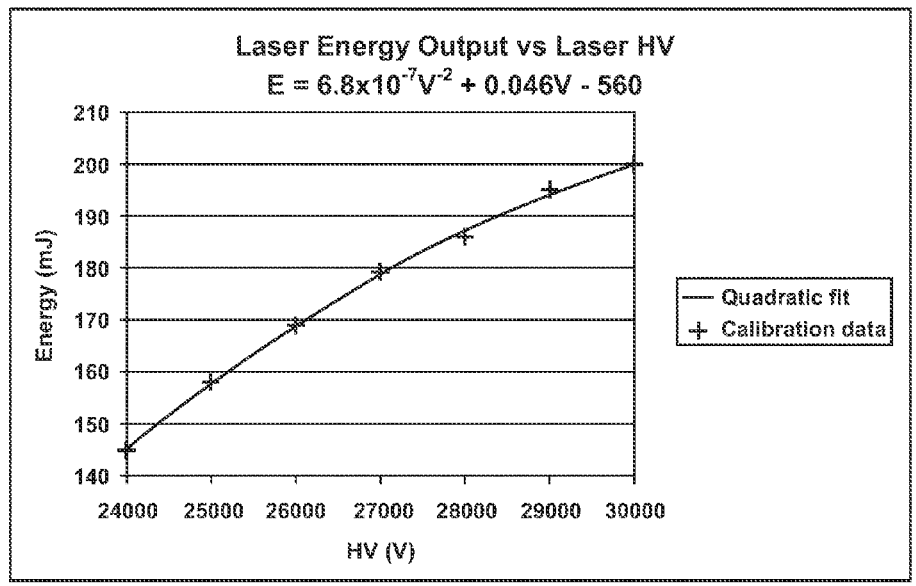
FIG. 6 graphically illustrates exemplary correlation data between pulse energies and discharge high voltage, along with an associated correlation suitable for use in the systems and methods described herein.

Referring now to FIG. 6, an exemplary correlation between laser pulse energy and discharge high voltage is shown graphically. The "+"'s represent data obtained during the calibration series of laser firings, with the line representing the quadratic fit of the correlation. The differential of the curve fit or slope of the graph represents the rate of energy increase with respect to V, with this rate varying with differing Vs. The responsiveness of the laser is greater at lower values of V as indicated by the greater slope to the left side of the graph. If a particular energy increase is desired, then a relatively smaller increase in V may be employed at these lower voltages than when the voltages are greater so as to reside toward the right side of the graph. The processor will use the correlation information to calculate the V as described above. Alternative correlation forms may comprise look-up tables and interpolation routines, alternative curve fit equation forms (including polynomial, logarithmic, expansion series, splines, and the like), graphical data, or the like.

Figure 7:
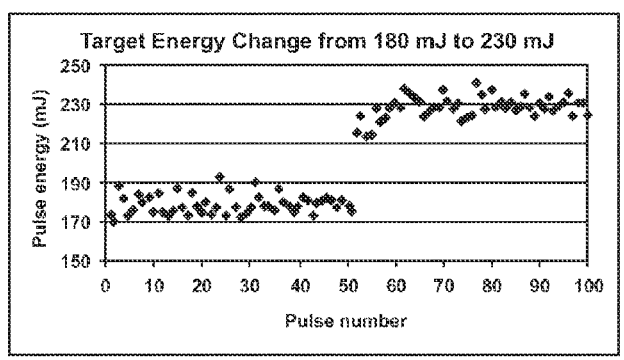
FIGS. 7 and 8 graphically illustrate output energy control in which operating characteristics of the laser are changed between pulses, with the changed characteristic here being target energy.
Figure 8:
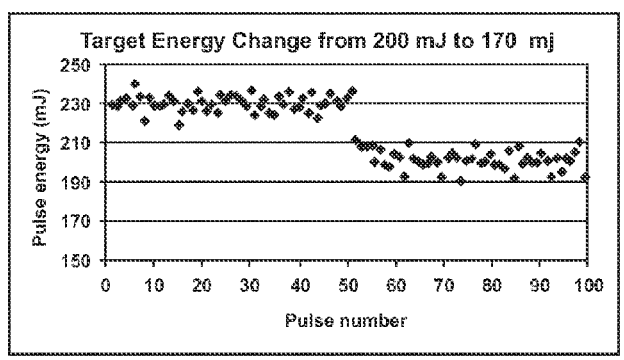

Referring now to FIGS. 7 and 8, the efficacy of the structures and devices described herein at controlling laser pulse energy can be demonstrated by implementing a step change in target energy of the laser system. The graph of FIG. 7 shows the changes in laser pulse energy that will result when the target energy changes from 180 mJ to 230 ml after about 50 pulses have been fired. FIG. 8 shows a similar change from 230 mJ to 200 ml after firing of about 50 pulses. Despite the change in target power, the laser pulse energy control system rapidly shifts the output of the laser with only a few pulses undershooting the target energy.

Figure 9:
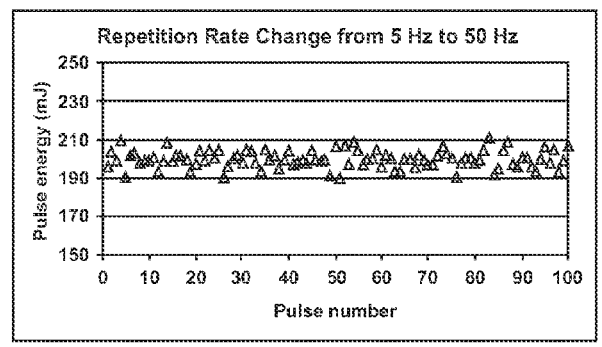
FIG. 9 graphically illustrates laser pulse energy control in which a firing rate of the laser is changed between pulses.

Referring now to FIG. 9, efficacy of the laser pulse energy control described herein may also be shown by keeping the target energy of the laser fixed (here at 220 ml), and by changing the firing rate (here from 5 Hz to 50 Hz after about 50 pulses). The lack in change in mean energy despite the repetition or firing rate change indicates that the system can accommodate changes in laser firing rate without significantly decreasing the accuracy of the laser eye surgery treatment.

Figure 10A:
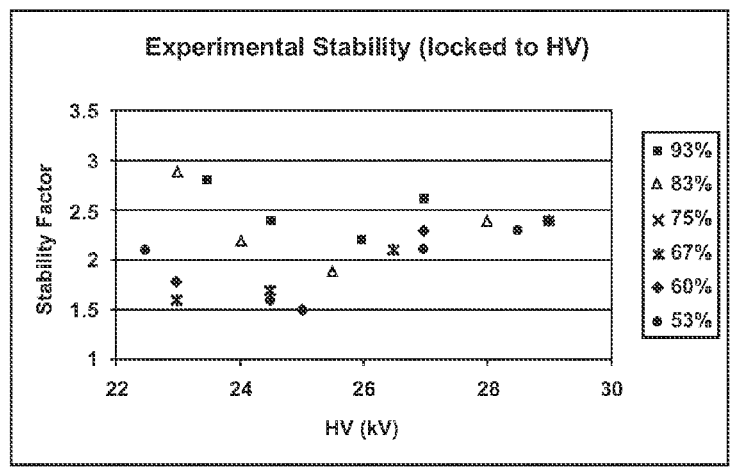
FIGS. 10A-10D graphically illustrate exemplary laser pulse energy stability under differing operating characteristics.
Figure 10B:
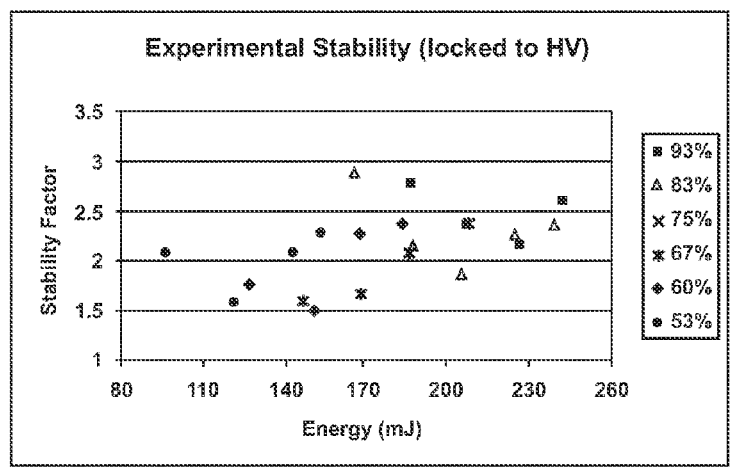

Referring now to FIGS. 10A and 10B, shot-to-shot noise and system stability may be analyzed by first running the system with the drive circuit set at a fixed or constant discharge high voltage under a variety of operating conditions, and then running the system with the discharge high voltage being set per the control methodologies described herein. So as to model the use of a laser at various operating conditions, six different gas mixes may be employed, with each gas mixture including a percentage of premix in the excimer laser chamber as indicated in the graph. A calibration mode may be run for each gas mixture and the response analyzed using the system hardware and software.

Sets of 1,000 pulses were fired with the laser set at a constant voltage and pulse energies were recorded, so as to generate data illustrated in FIG. 10A. The total pressure in the laser chamber was about 2,950 mb for all runs. The laser energy noise from the constant high voltage runs were then used as an input parameter for a computer simulation of the output energy control run, with the noise levels being set for a particular constant high discharge voltage run as being equal to input noise levels for running the laser with the variable voltage control methodology at approximately the same voltage.

In the graphs of FIGS. 10A-10D, the stability factor refers to the standard deviation of the energy of the pulses divided by their mean, expressed as a percentage. The noise level for constant V runs are summarized in FIG. 10A, while the same data is presented in FIG. 10B plotted against the average energy of the run. Generally, it can be seen that the laser runs with less shot-to-shot noise at lower values of V and with smaller percentages of premix.

Figure 10C:
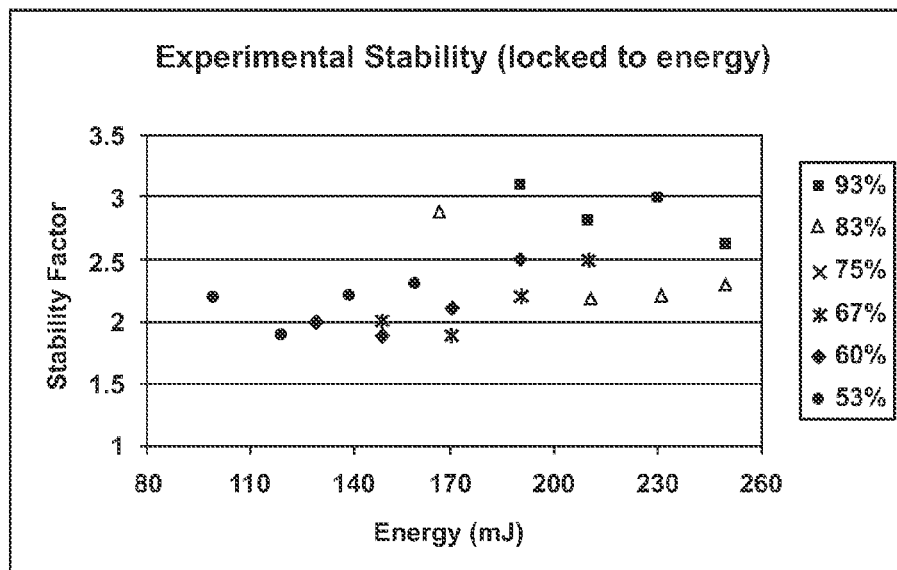
Figure 10D:
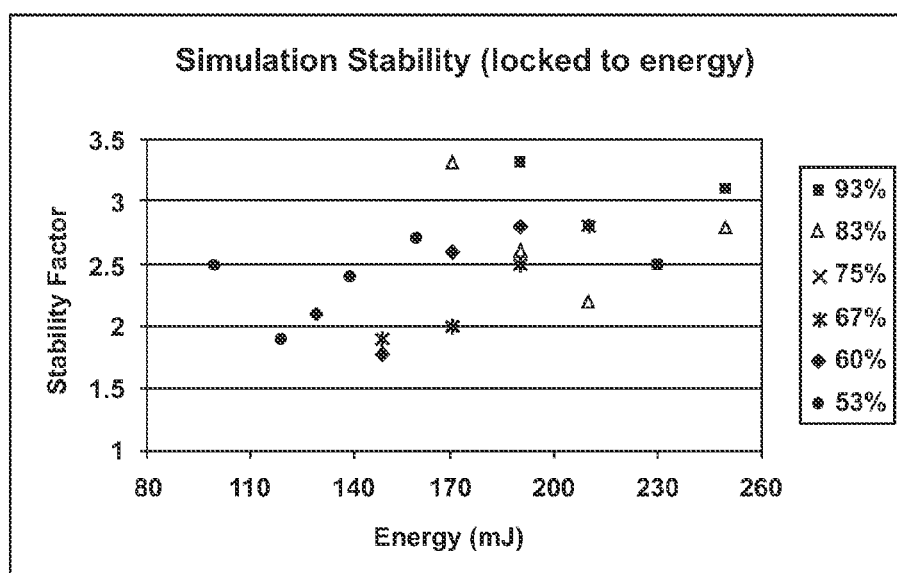

Referring now to FIGS. 10C and 10D, data for the laser as it might run with active control of the discharge high voltage as described above, is presented in FIG. 10C. There may be a small increase in the noise level when actively controlling the high discharge voltage, which appears reasonable.

The noise levels identified in FIG. 10C may be simulated using (for example) an Excel™ spreadsheet. Such an analysis may take as an input the noise levels obtained when the energy is produced with the laser set at a fixed high discharge voltage, along with the parameters $c_1$, $c_2$, and $c_3$ obtained during the calibration mode.

FIG. 10D shows additional representative data from such a simulation. The simulation data of FIG. 10D provides a reasonable representation of laser behavior, considering that shot-to-shot noise is a random process, so that experiments in simulation can only be expected to converge after experimentation and simulation are repeated. Nonetheless, the simulation may provide insight into known laser behaviors. Data obtained using actual excimer lasers may be analyzed and simulations run for extreme conditions, with the simulations preferably predicting that no identified circumstances result in unstable energy oscillation or the like.

While the exemplary embodiments have been described in some detail, for clarity of understanding and by way of example, a variety of modifications, adaptations, and changes may be obvious to those of skill in the art. Hence, the scope of the present invention is limited solely by the appended claims.

What is claimed is:

1. A method for controlling a pulsed laser, the method comprising:

firing the laser to produce a series of laser pulses, each pulse fired by applying an associated voltage of the laser, wherein the laser comprises an excimer laser, and wherein the series of pulses are fired by applying at least four differing voltages to the laser while the laser is operating in a calibration mode and prior to transmitting pulses onto a target surface;

measuring energies of each laser pulse of the series of laser pulses;

generating a correlation between the measured energies of the pulses and the associated voltages of the laser, the correlation defining differing rates of change in pulse energy with changes in voltage;

generating a first laser pulse by applying a first voltage to the laser;

measuring a first energy of the first pulse;

determining a second voltage for the laser so as to generate a second pulse with a desired pulse energy using the correlation and the measured first energy of the first pulse; and firing the laser by applying the second voltage so as to produce the second pulse;

wherein the first and second laser pulses are directed onto the target surface while the laser is in an operating mode, wherein a firing rate of the laser varies while the laser is in the operating mode, and wherein the laser remains in the operating mode for less than about 10 minutes; and wherein the second voltage, Vnew, is calculated from the first voltage, Vold, using a damping factor D and a desired change in energy $\Delta E$ between the energy of the first pulse and the desired energy according to an equation:

$$V_{new} = V_{old} + D(\Delta E/(2c_1 V_{old} + c_2))$$

In which generating a correlation comprises identifying constants $c_1$ and $c_2$.

2. The method of claim 1, wherein the correlation comprises a quadratic relationship between a pulse energy E and a discharge high voltage V of the laser of the form $$E = c_1 V^2 + c_2 V + c_3$$

in which $c_1$, $c_2$, and $c_3$ are constants.

3. The method of claim 1, wherein the second voltage is determined by identifying a desired change in energy $\Delta E$ between the energy of the first pulse and the desired energy, and by identifying an appropriate change in voltage from the correlation using the first voltage.

4. The method of claim 1, further comprising damping variations in the voltage according to a damping factor.

5. The method of claim 1 wherein the series of pulses comprises a plurality of pulses at each voltage, and further comprising averaging the pulse energies at each voltage, the correlation being determined using the averaged pulse energies.

6. The method of claim 1, wherein the target surface is disposed on a corneal tissue, the operating mode effecting resculpting of the corneal tissue so as to alter optical characteristics of the eye, and wherein the laser is operated in the calibration mode prior to treatment of each of a plurality of patients.

* * * * *